(12) United States Patent
Kosinski

(10) Patent No.: US 8,007,475 B2
(45) Date of Patent: Aug. 30, 2011

(54) POSITIVE DISPLACEMENT FLUSH SYRINGE

(75) Inventor: Anthony J. Kosinski, New Providence, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 935 days.

(21) Appl. No.: 10/594,335

(22) PCT Filed: Jan. 7, 2005

(86) PCT No.: PCT/US2005/000624
§ 371 (c)(1),
(2), (4) Date: Apr. 17, 2007

(87) PCT Pub. No.: WO2005/070485
PCT Pub. Date: Aug. 4, 2005

(65) Prior Publication Data
US 2007/0179452 A1    Aug. 2, 2007

Related U.S. Application Data

(60) Provisional application No. 60/535,557, filed on Jan. 9, 2004.

(51) Int. Cl.
*A61M 5/00* (2006.01)
*A61M 5/315* (2006.01)
(52) U.S. Cl. ........ 604/191; 604/218; 604/219; 604/220; 604/222

(58) Field of Classification Search .......... 604/218–220, 604/500, 191
See application file for complete search history.

(56) References Cited

U.S. PATENT DOCUMENTS

| | | | | |
|---|---|---|---|---|
| 4,312,344 A * | 1/1982 | Nilson | ........................... | 604/212 |
| 4,500,310 A * | 2/1985 | Christinger | .................... | 604/228 |
| 5,411,488 A * | 5/1995 | Pagay et al. | .................... | 604/218 |
| 5,496,285 A * | 3/1996 | Schumacher et al. | ........ | 604/218 |
| 5,620,423 A * | 4/1997 | Eykmann et al. | ............. | 604/219 |
| 5,795,337 A * | 8/1998 | Grimard | ........................ | 604/222 |
| 6,644,309 B2 * | 11/2003 | Casper et al. | ............ | 128/203.21 |
| 6,796,217 B2 * | 9/2004 | Horita et al. | ..................... | 92/240 |
| 7,087,037 B2 * | 8/2006 | Chiba et al. | ..................... | 604/38 |
| 2005/0063857 A1 * | 3/2005 | Alheidt et al. | .................. | 422/28 |

* cited by examiner

*Primary Examiner* — Nicholas D Lucchesi
*Assistant Examiner* — Ian K Holloway
(74) *Attorney, Agent, or Firm* — Jeanne P. Lukasavage; Diehl Servilla LLC

(57) ABSTRACT

A flush syringe assembly comprises a barrel including a cylindrical side wall having an inside surface defining a chamber for retaining fluid, an open proximal end and a distal end including an elongate tip extending distally therefrom having a passageway in fluid communication with the chamber. A plunger including an elongate body portion has a stopper at its distal end. The stopper is slidably positioned in fluid-tight engagement with the inside surface of the barrel for driving fluid out of the chamber. The distal end of the stopper is configured to collapse while fluid is being driven though the passageway through motion of a plunger and to continue to drive fluid through the passageway after motion of the plunger has stopped.

23 Claims, 15 Drawing Sheets

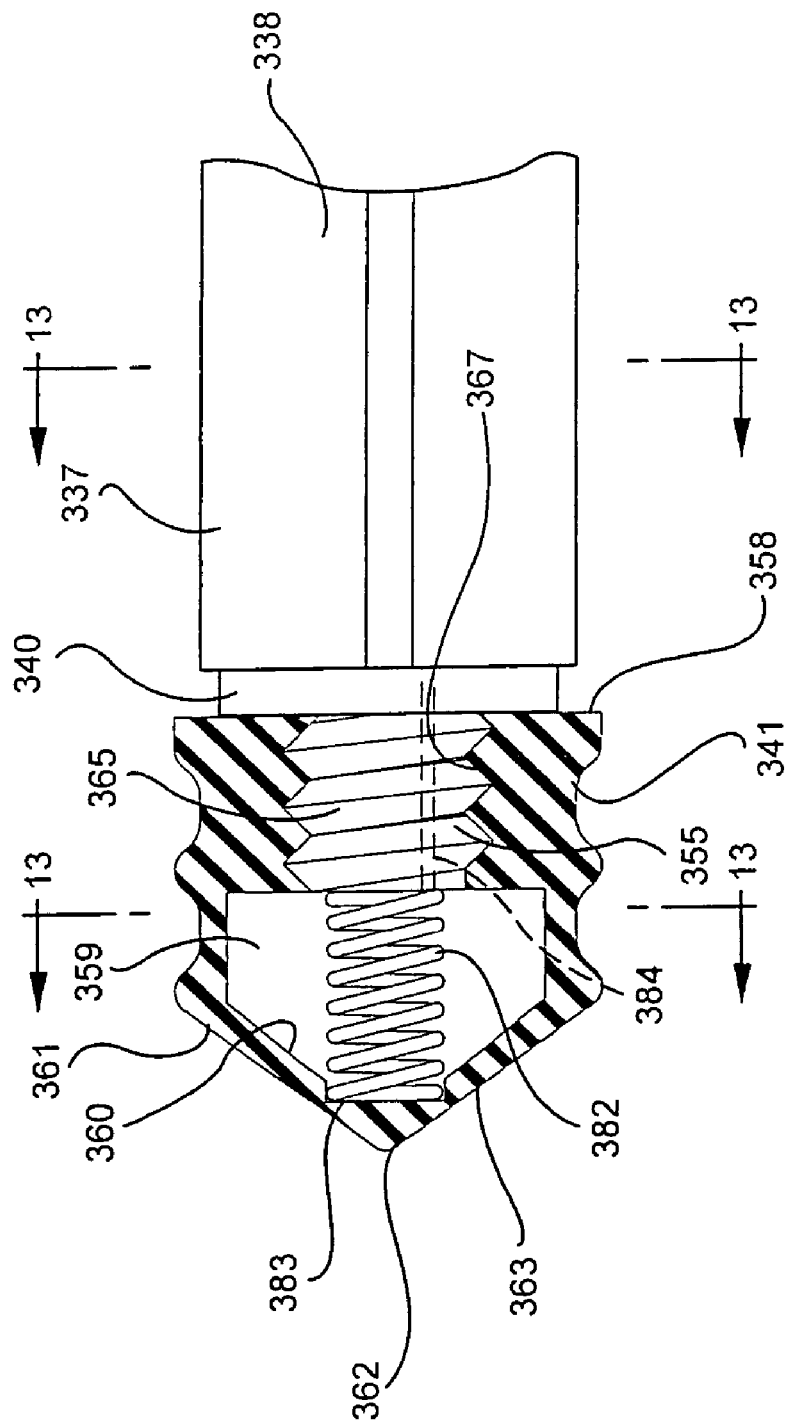

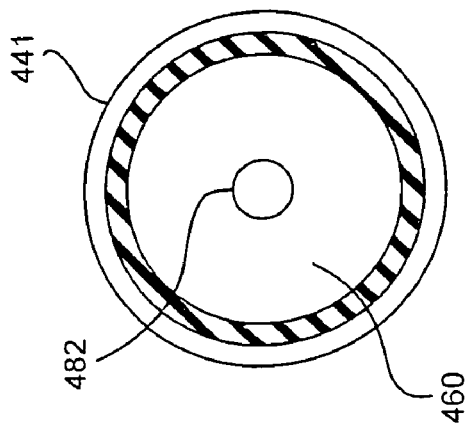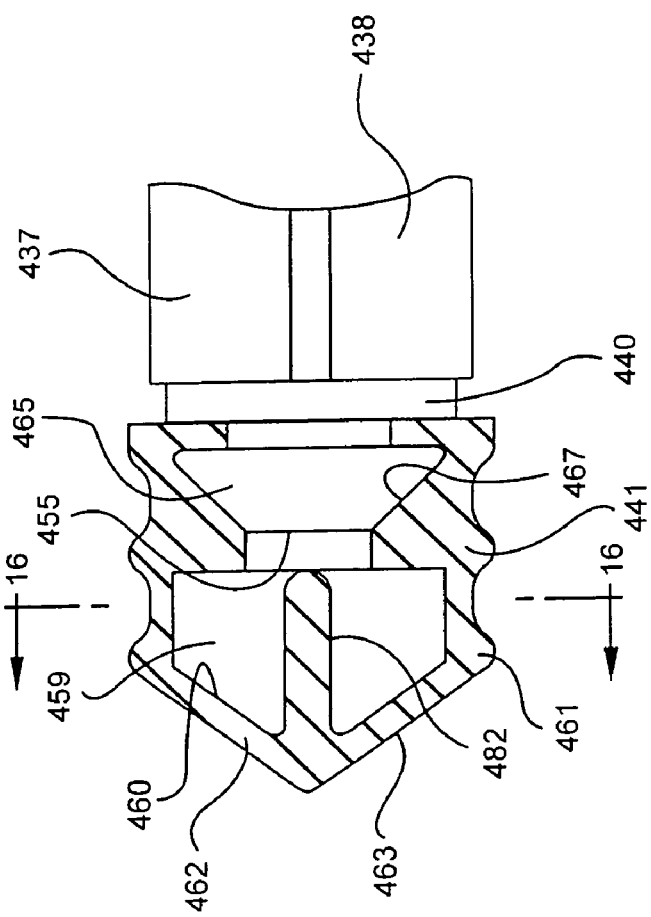

ized flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 to 20 ml. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V. port or clamp the I.V. line. Either technique maintains positive pressure on the fluid in the VAD to prevent reflux of fluid and blood.

POSITIVE DISPLACEMENT FLUSH SYRINGE

This application claims priority from U.S. provisional application No. 60/535,557 filed Jan. 9, 2004.

BACKGROUND OF THE INVENTION

The present invention relates to syringe assemblies and particularly to, syringe assemblies for use in flush procedures, for vascular access devices (VAD's).

VAD's are commonly used therapeutic devices. There are two general classifications of VAD's, peripheral catheters and central venous catheters. If not properly maintained, VAD's can become occluded. To ensure VAD's are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 to 20 ml. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V. port or clamp the I.V. line. Either technique maintains positive pressure on the fluid in the VAD to prevent reflux of fluid and blood.

For flush procedures, the I.V. line refers to a system containing a VAD, tubing set with clamp and may terminate with a port or valve. The most common types of I.V. ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula in order to infuse fluids or to withdraw fluids from the catheter. Upon withdrawal of the needle cannula the septum seals itself. Ports having pre-slit septums are used with blunt cannula or the frusto-conically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frusto-conically shaped tip of a syringe barrel to allow fluid communication between the interior of the syringe and the catheter. These valves may contain structure for delivering fluid from a storage compartment in the valve to the catheter, and are referred to in the art as positive displacement valves. Such a valve is taught in U.S. Pat. No. 6,206,861B1. Positive displacement valves were developed to overcome the reflux caused by the disconnection of a syringe tip or cannula from a port or valve. Unfortunately, the positive displacement valves were not designed to compensate for the worst-case syringe stopper induced reflux. When using a traditional syringe assembly containing an elastomeric stopper, the stopper is often compressed when it contacts the distal end of the syringe barrel at the completion of the flush procedure. If the user releases the pressure on the plunger after the flush solutions is delivered, the compressed stopper may expand back to its normal size drawing fluid back into the catheter. This fluid is referred to as syringe stopper induced reflux. Traditional syringe assemblies were designed to accurately deliver medications. Traditional syringe assemblies supplied by various suppliers may appear similar but can vary significantly in terms of performance especially stopper induced reflux. Because the catheter is inserted into the patient the users cannot see the reflux when it occurs and therefore cannot take corrective actions to address a potential problem.

Disconnection induced reflux and syringe stopper induced reflux would not be an issue if all users practice the positive pressure flushing techniques described hereinabove every time they flushed a VAD. However, user experience, environmental circumstance and patient condition vary significantly within the hospital setting and even more when one considers other areas that flush procedures are performed such as clinics and home care. As a result, VAD's are frequently occluded resulting in the need for additional professional time, declotting drugs, removal of catheters and new procedures to place new catheters. All of these interventions come at a cost to the healthcare system and its patients. It is desirable to have syringe assemblies that are designed for flush procedures to enhance best clinical practice. Specifically, syringe assemblies that are configured to automatically minimize or eliminate reflux without depending entirely on user technique. Further, the prior art focuses on syringe assemblies designed to deliver medications and not syringe assemblies that automatically provide additional small amount of flush solution in the I.V. line at the completion of the flush procedure.

Therefore there is a need for a simple, straight forward, automatic, easy-to-manufacture syringe assembly which helps reduce or eliminate reflux of blood into the catheter during and after the flush procedure has occurred even if recommended flush procedure techniques are not precisely followed. For example, prematurely releasing the compressive force on the plunger and/or removing the syringe from the I.V. line before it is clamped may cause reflux of blood into the catheter, thus increasing the chance of VAD occlusion.

SUMMARY OF THE INVENTION

The present invention is directed to a syringe assembly for use in flush applications. The syringe assembly has structure to provide an additional positive displacement of flush solution after the flush solution has been substantially delivered from the cavity in the syringe barrel through the application of an additional distally-directed force provided by the stopper.

A flush syringe assembly comprises a barrel including a cylindrical side wall having an inside surface defining a chamber for retaining fluid, an open proximal end and a distal end including a distal wall with a tip extending distally therefrom having a passageway therethrough in fluid communication with the chamber. A plunger including an elongate body portion having a proximal end, a distal end and a stopper slidably positioned in fluid-tight engagement with the inside surface of the barrel for driving fluid out of the chamber by movement of the stopper relative to the barrel is provided. The elongate body portion of the plunger extends outwardly from the open proximal end of the barrel. Structure is provided for moving fluid distally in the passageway after fluid has been delivered from the chamber and the distal motion of the plunger with respect to the barrel has stopped. The structure for moving fluid after motion of the plunger has stopped may include the stopper having a distal end with a distal wall and a cavity therein defining an inside surface, and a proximal end. The distal wall of the stopper is flexible enough to collapse at least partially into the cavity under the liquid pressure of a flush procedure and to move back toward its original shape at the completion of the flush procedure to force additional fluid into the passageway. The distal wall of the stopper desirably deflects at least partially into the cavity when the liquid pressure in said chamber is about 5 mm Hg (0.1 psi) or more.

When the syringe assembly of the present invention is attached to a peripheral catheter the amount of fluid moving distally in the passageway after distal motion of the plunger with respect to the barrel has stopped, is about 0.001 ml or more.

It is also desirable that the desired volume of additional fluid, when the syringe assembly is connected to a peripheral catheter, be delivered in a time of 0.5 second or more. It is preferable that the additional fluid be delivered in a time of about 2.5 seconds or more.

A distal tip on the distal end of the plunger may be connected to the stopper. The stopper may include a conically-shaped distal surface and the barrel may include a conically-shaped inside surface at its distal wall.

The syringe assembly may further include a spring at the inside surface of the cavity in the stopper. The spring is configured to compress when the stopper is in its collapsed position and to urge the distal wall of the stopper from the collapsed position toward its original shape. The spring may be a coil spring.

The syringe assembly may also include the inside surface of the stopper having a proximally directed projection configured to compress when the stopper is in its collapsed position and to urge the distal wall of the stopper from its collapsed position toward its original shape.

The syringe assembly may also include the stopper having at least one and preferably a plurality of raised ribs on its inside surface configured to deflect through tension, compression or combinations thereof when the stopper is in a collapsed position and to urge the distal wall of the stopper from its collapsed position toward its original shape.

The syringe assembly may further include the distal wall of the stopper having an area of reduced thickness to lower the pressure required for the distal wall to collapse. The area of reduced thickness may include a circular groove in the inside surface of the distal wall of the stopper.

The distal tip of the plunger may include venting structure such as an aperture therein communicating with the cavity in the stopper to allow air trapped in the stopper to escape when the stopper collapses and to enter the cavity when the stopper returns to its original shape.

The syringe assembly may also include flush solution in the chamber and a tip cap releasably connected to the tip of the syringe barrel for sealing the passageway. The flush solution may be selected from the group consisting of saline flush solution and heparin lock solution.

The syringe assembly may further include a needle assembly including a cannula having a proximal end, a distal end, and a lumen therethrough. A hub having an open proximal end containing a cavity and a distal end attached to the proximal end of the cannula so that the lumen is in fluid communication with the cavity of the hub. The needle assembly is removably attached to the tip of the barrel through engagement of the tip to the cavity of the hub so that the lumen is in fluid communication with the chamber of the barrel.

The stopper may be made of material selected from the list consisting of thermoplastic elastomers, natural rubber, synthetic rubber, thermoplastic materials and combinations thereof.

BRIEF DESCRIPTION OF THE DRAWINGS

FIG. 12 is a partially cross-sectioned side-elevational view of another alternative embodiment of the plunger and stopper of the flush syringe assembly.

FIG. 15 is a partially cross-sectioned side-elevational view of another alternative embodiment of the plunger and stopper of the flush syringe assembly.

FIG. 16 is a cross-sectional view of the stopper of FIG. 15 taken along line 16-16.

DETAILED DESCRIPTION

Figure 1:
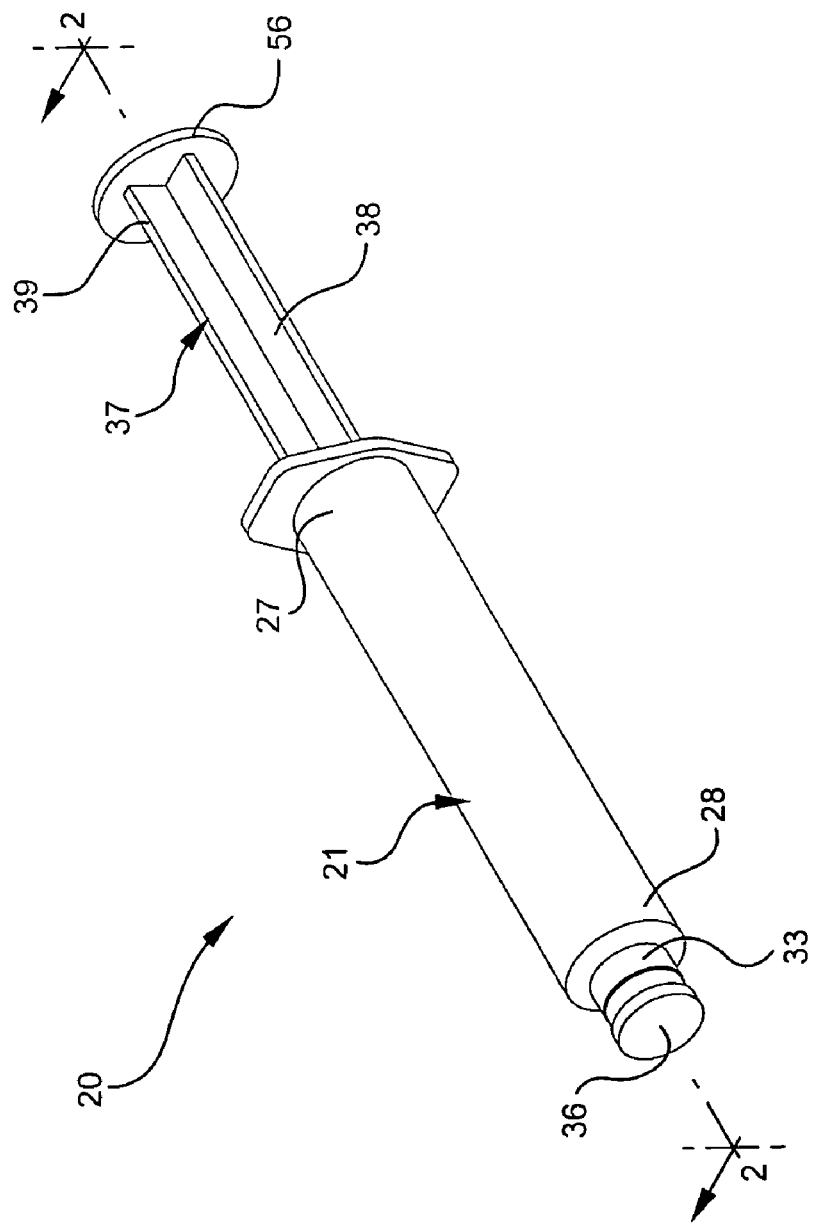
FIG. 1 is a perspective view of a syringe assembly of the present invention.
Figure 2:
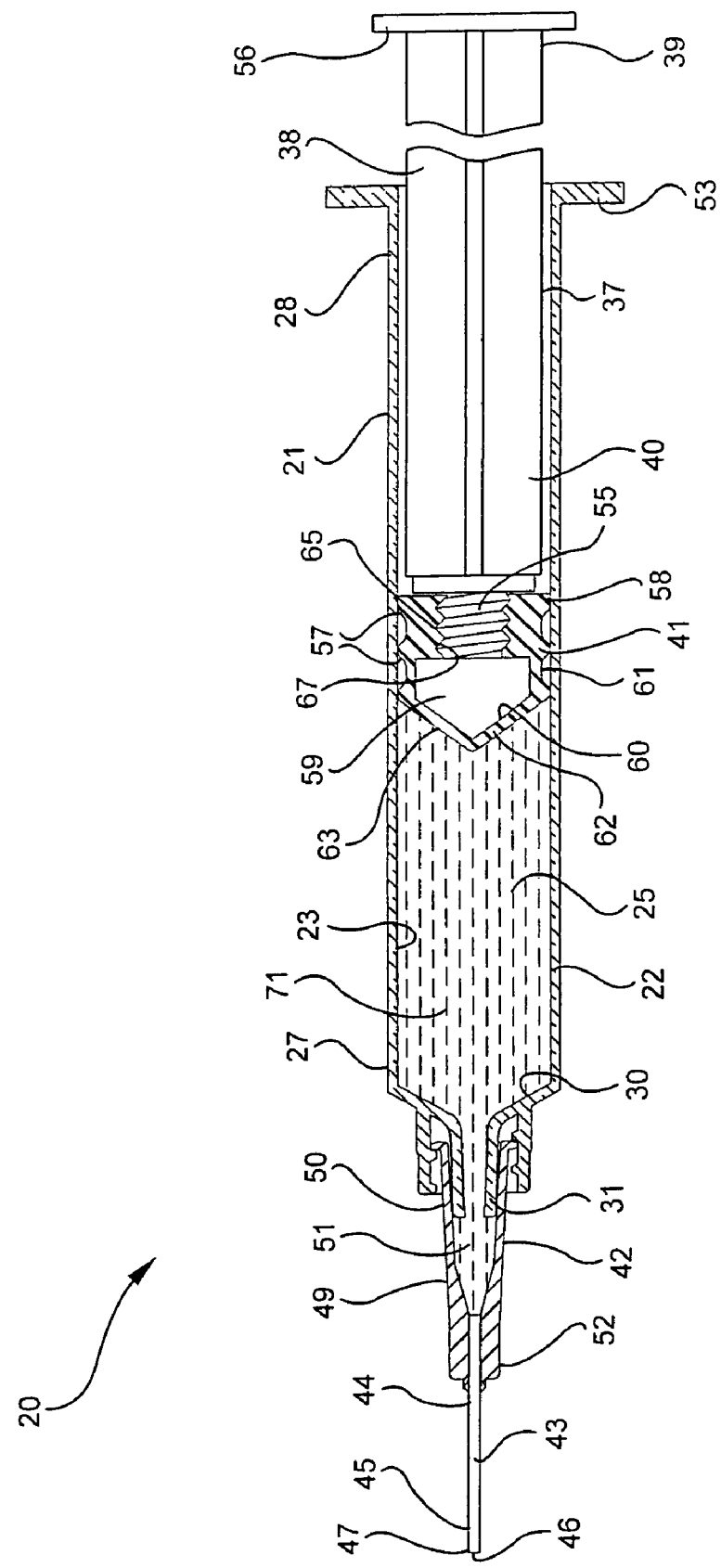
FIG. 2 is an enlarged partially cross-sectioned side elevational view of the syringe assembly of FIG. 1 with a needle assembly attached.

Referring to FIGS. 1-7, a syringe assembly 20 according to the present invention generally comprises a barrel 21, including a cylindrical sidewall 22 having an inside surface 23 defining a chamber 25 for retaining fluid. The barrel further includes an open proximal end 27 and a distal end 28 having a distal wall 29 with an elongate tip 31 extending distally therefrom and having a passageway 32 therethrough in fluid communication with the chamber. The inside surface of the barrel at the distal wall, indicated as 30, is preferably conically shaped. The distal end of the barrel preferably, but not necessarily, includes a locking luer type collar 33 concentrically surrounding tip 31. The collar includes an inside surface 34 having at least one thread 35 thereon.

A cannula 43 includes a proximal end 44, a distal end 45 and a lumen 46 therethrough. The distal end of the cannula may include a sharp tip or a blunt tip 47 as shown. The cannula may be connected directly to the tip of the syringe barrel to establish fluid communication between the lumen and the chamber. Also, the cannula may be part of a needle assembly 42 including a hub 49 having an open proximal end 50 containing a cavity 51 and a distal end 52 attached to the proximal end of the cannula so that lumen of the cannula is in fluid communication with the cavity. The cavity of the hub can be removably frictionally engaged to the tip of the barrel.

A plunger 37 includes an elongate body portion 38, a proximal end 39 and a distal end 40. A stopper 41 is disposed at the distal end of the plunger rod through a structure that will be described in more detail hereinafter. Stopper 41 includes at least one rib and preferably a plurality of ribs 57 on its outside diameter. The stopper is slidably positioned in fluid-tight engagement with the inside surface of the barrel for drawing fluid into and driving fluid out of the chamber by movement of the stopper relative to the barrel. If the syringe assembly is prefilled from the manufacturer, the stopper need not be used for or able to draw fluid into the barrel. Elongate body portion of the plunger extends outwardly from the open proximal end of the barrel. Stopper 41 includes a distal end 61 having a distal wall 62 defining a cavity 59 therein having an inside surface 60. The stopper further includes a distal surface 63 and a proximal end 58.

The syringe assembly includes structure for moving fluid distally in passageway 31 after fluid has been delivered from chamber 25 and the distal wall of the stopper is in contact with the distal wall of the barrel.

The structure for moving fluid distally in the passageway after fluid has been delivered from the chamber includes stopper 41 preferably being connected to distal tip 55 on the plunger. If the cavity in the stopper is open to the proximal end than the plunger rod should be connected to the stopper so that the distal tip does not fill the cavity in the stopper. In this embodiment, the stopper and the plunger are connected through the action of an external thread 65 on the distal tip and internal thread 67 in the stopper cavity. There are numerous ways to connect the stopper and plunger, if required, including a snap-fit arrangement described hereinbelow, adhesives, fasteners, ultrasonic welding, two stage molding and the like. The distal tip can engage the exterior of the stopper rather than the interior or just the proximal end of the stopper. All of these various structures for connecting a stopper to a plunger are within the purview of the present invention and the threaded engagement described in this embodiment is merely illustrative of these many possibilities. In this preferred embodiment distal surface 63 of the stopper is conically shaped and inside surface 23 of barrel 21 at distal wall 29 is also conically shaped.

An important aspect of the present invention is that distal wall 62 is structured to be flexible enough to collapse at least partially into the stopper cavity under the liquid pressure of a flush procedure and strong enough to move back toward its original shape at the completion of the flush procedure to force additional flush solution into the passageway of the barrel as will be described in more detail hereinafter. The term "collapse" as used herein is intended to refer to deflection of the stopper distal wall toward the stopper cavity. The shape and extent of the deflection of the stopper will vary with the various configurations of the stopper and plunger.

The stopper may be made of any material suitable for providing sealing characteristics while under compression. For example, the stopper may be made of thermoplastic elastomers, natural rubber, synthetic rubber or thermoplastic materials and combinations thereof. The stopper may be integrally formed or composed of separate components of the same or different materials joined together. The plunger in this embodiment is preferably made of material which is more rigid than the stopper such as polypropylene, polyethylene and the like. Materials should be chosen to be compatible with the sterilization procedure being used.

In operation, syringe assembly 20 is connected to a needle assembly and filled with flush solution using known methods. Also, the syringe assembly may be provided pre-filled from the manufacturer or supplier. The flush solution may be any solution intended for flushing or maintaining the performance of VAD's. It is preferred that the flush solution be selected from the group consisting of saline flush solution and heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml. The syringe with needle assembly attached is used to pierce the pierceable septum or a blunt cannula may be inserted into a pre-split septum of a vial or neck of a glass ampoule containing flush solution and the flush solution is drawn into the syringe barrel by pulling plunger flange 56 in the proximal direction while holding barrel 21, to draw fluid through the needle cannula into fluid chamber 25.

Alternatively, large quantities of flush syringes may be pre-filled with flush solution during or after the assembly of the syringe using sterile filling methods. Such prefilled syringes may be supplied with a tip cap, such as tip cap 36 releasably connected to tip 31 sealing passageway 32. It is preferred that the tip cap is formed of material selected from a group of thermoplastic materials and elastomeric materials such as natural and synthetic rubber, thermoplastic elastomers or combinations thereof.

Figure 6:
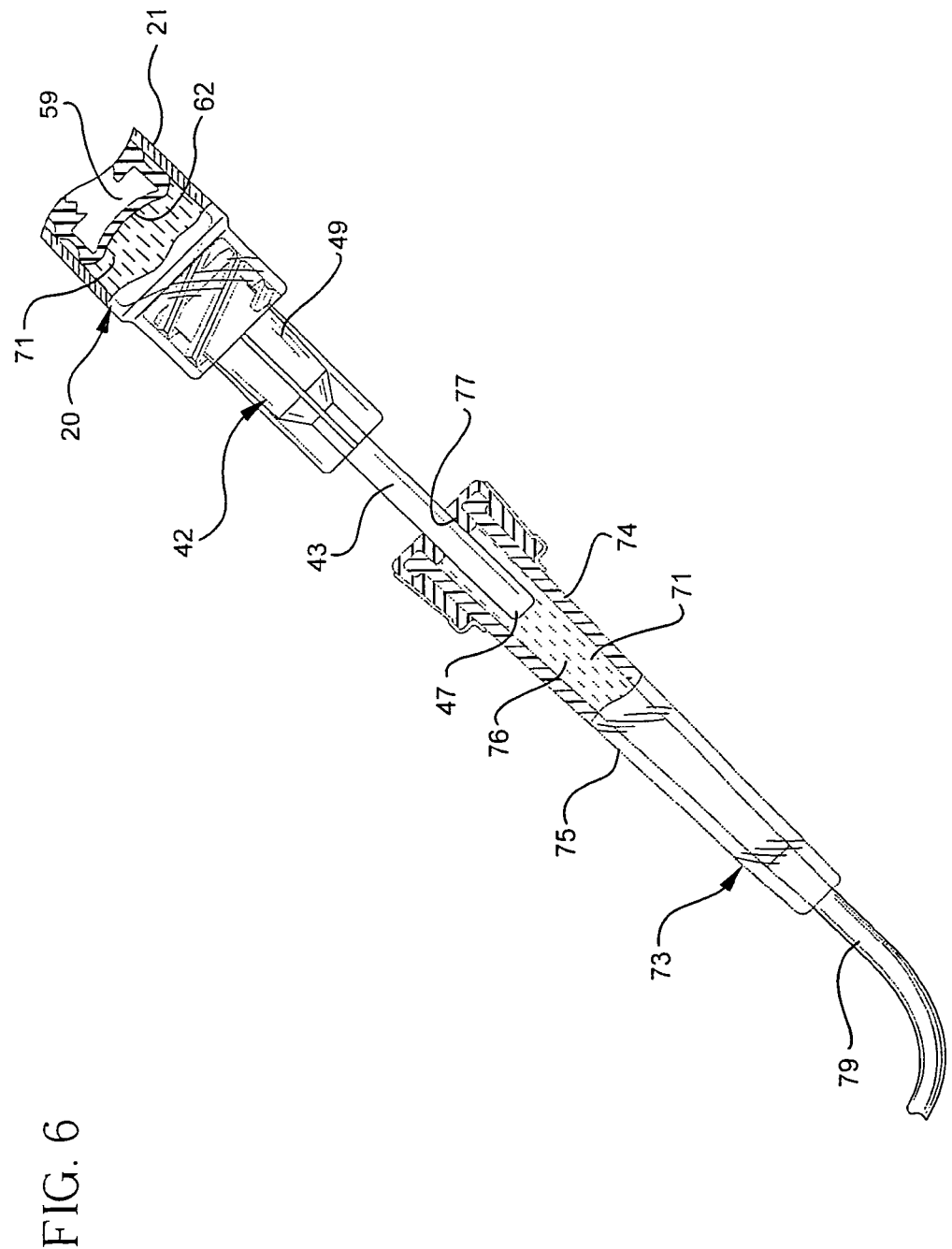
FIG. 6 is a side-elevational view illustrating the syringe assembly in use with a catheter injection site.

The syringe is now ready for use in flushing a VAD such as a catheter of an I.V. set. I.V. sets can be very complicated and may include multiple injection ports, a valve and/or other components. For the purpose of illustrating the present invention a simplified I.V. set 73 is illustrated in FIG. 6. I.V. set 73 comprises an I.V. site 74 which includes a housing 75 having a hollow interior 76 and a septum 77 at its proximal end. An I.V. line 79 having a conduit therethrough extends from the distal end of the housing. I.V. line 79 may be a catheter or be connected to a catheter at its distal end. For this I.V. set, septum 77 is pre-slit for use with blunt cannula. The I.V. site may be a valve having structure for accepting the syringe barrel tip and being activated by the insertion of the tip to establish fluid communication with the catheter, such as the valve taught in U.S. Pat. No. 6,171,287.

As previously mentioned, there are two general classifications of VAD's, peripheral catheters and central venous catheters. Peripheral catheters are used to access veins in the peripheral extremities such as the hand and arm. Peripheral catheters are relatively short in length ranging from about 14 mm to 48 mm in length, and are available in gauge sizes from about 16 to 24. It is believed that the most commonly used peripheral catheters are 20 gauge having an ID of about 0.81 mm (0.032 inch) and 22 gauge having an ID of about 0.66 mm (0.026 inch), and having a length of about 25 mm to 32 mm. As used herein, the term "peripheral catheter" is intended to refer to a 20 or 22 gauge catheter having a length of about 25 mm. Central venous catheters are substantially longer than peripheral catheters and are inserted in the patient and terminate near the heart.

Figure 3:
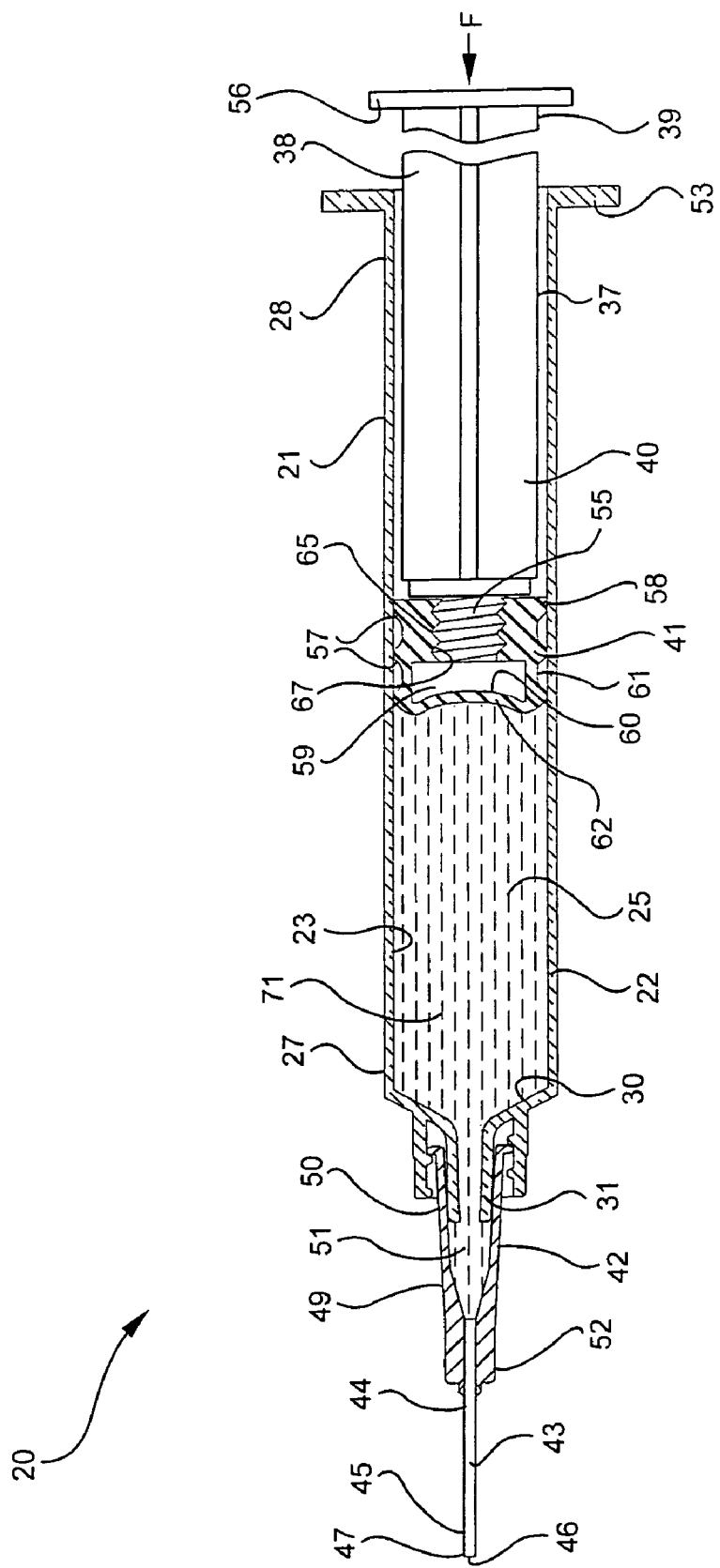
FIG. 3 is an enlarged partial cross-sectional side elevation view of the syringe assembly of FIG. 2 shown during the flush procedure.

FIG. 3 illustrates syringe assembly 20 during a flush procedure wherein force F is being applied to flange 56 of the plunger forcing flush solution 71 from the chamber through passageway 32 and through the lumen of the cannula through a catheter and into the patient's vein. It should be noted that the pressure on the flush solution during the flush procedure is higher than the patient's venous blood pressure (which is believed to be about 10 mm Hg or less) where the catheter enters the blood vessel, so that fluid moves through the catheter toward the vein. This higher pressure causes distal wall 62 of the stopper to collapse into cavity 59 of the stopper while the plungers is being advanced in a distal direction within the barrel. It is desired that the distal wall collapse under fluid pressure in the chamber of about 5 mm Hg (0.1 psi) or more.

With the syringe connected to a peripheral catheter, it is preferred that the distal wall of the stopper deflect enough during the flush procedure to deliver an additional 0.001 ml or more of liquid when the flush procedure is completed and distal motion of the plunger with respect to the barrel has stopped. A stopper configured to collapse at about 5 mm Hg (0.1 psi) and to force about 0.001 ml or more of liquid from the barrel toward a peripheral catheter after a flush procedure, in about 0.5 second or more is desirable wraith about 2.5 seconds or more being preferred. However, a wide variation in these pressure, displacement and volume parameters can be used to accomplish the desired result. The individual parameters chosen may depend on the configuration and placement of the VAD, the syringe size and the flush solution being used.

Figure 4:
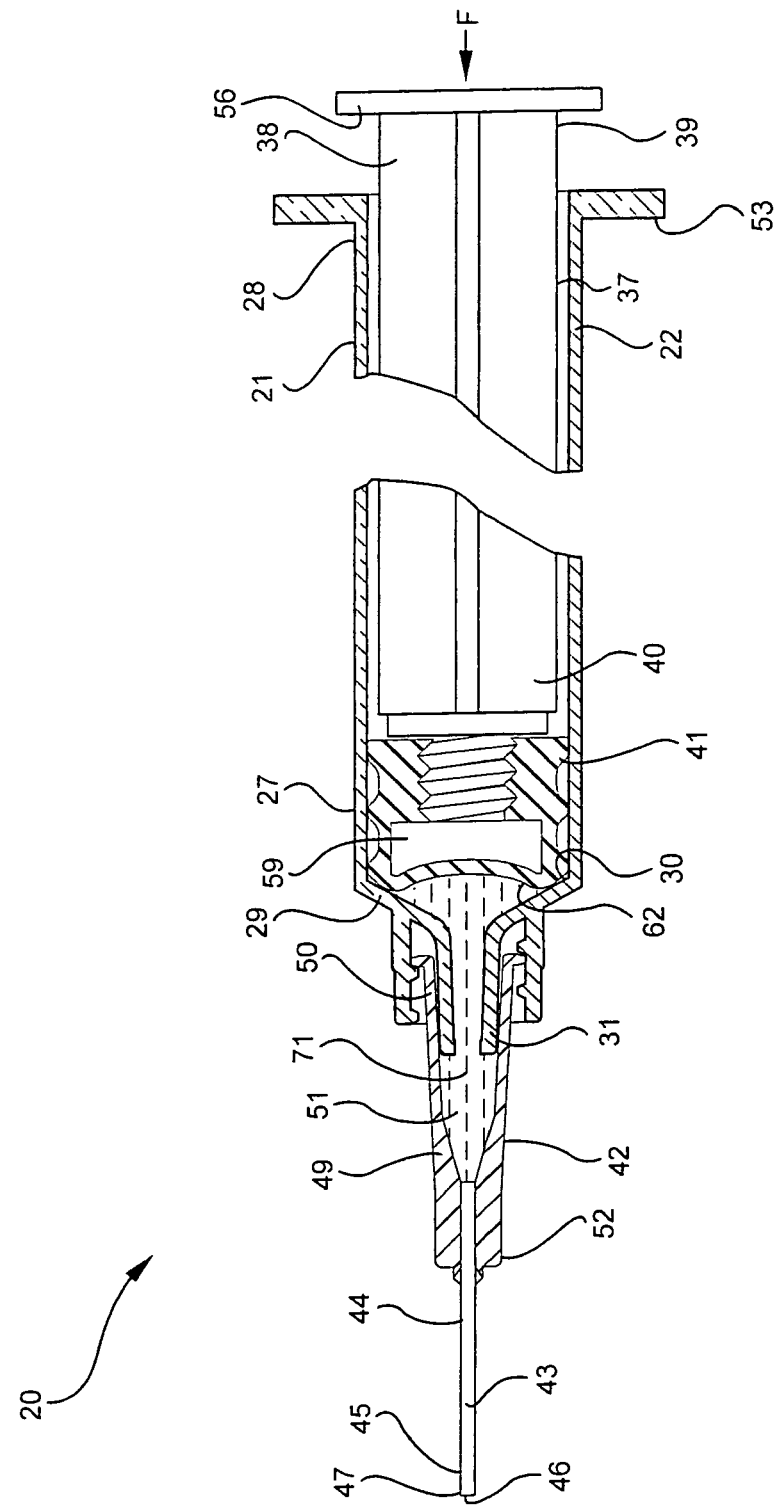
FIG. 4 is an enlarged partial cross-sectional side elevational view of the syringe assembly shown at the completion of flush solution delivery.
Figure 5:
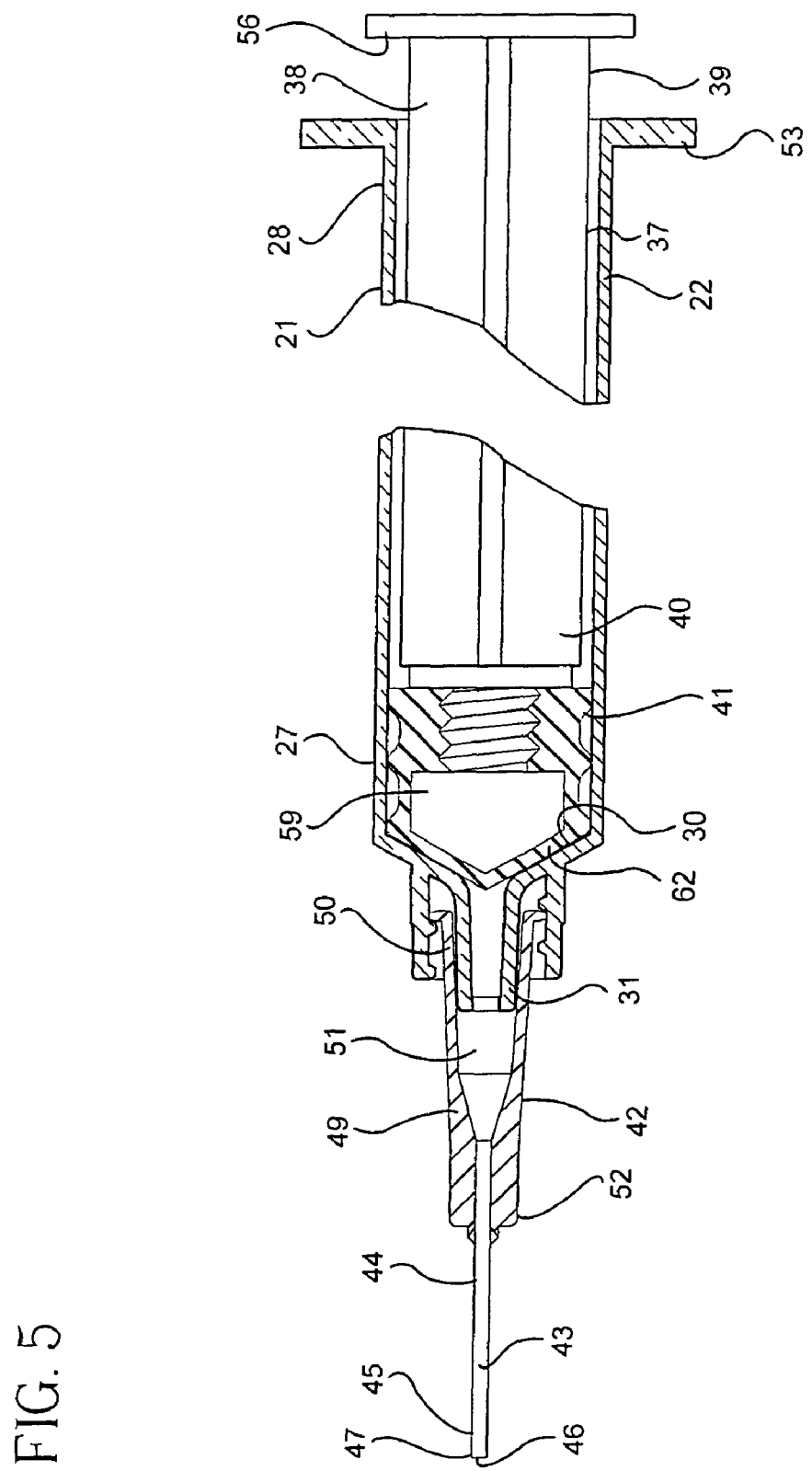
FIG. 5 is an enlarged partial cross-sectional side elevational view of the syringe assembly shown after the completion of flush solution delivery and after the stopper has driven an additional amount of flush solution through the barrel passageway.

Referring to FIG. 4, the position of the plunger and the stopper at the completion of the flush procedure is shown. At the completion of the flush procedure distal movement of the plunger relative to the barrel has stopped and, preferably, part of distal surface 63 of the stopper contacts inside surface 30 of the distal end wall of the barrel around the passageway sealing the passageway. At this point, while the user is clamping the I.V. line, distal wall 62 of the stopper is springing back toward its original shape, as illustrated in FIG. 5, and in doing so is forcing additional I.V. solution out of the chamber and through the passageway of the barrel. The positive displacement of fluid in the passageway in a distal direction will help prevent reflux while the I.V. line is being clamped and the syringe is being removed. After the I.V. line is clamped, the syringe assembly may be removed from the I.V. set. It should be noted that removing a syringe from an I.V. set can promote reflux by the withdrawal of solid elements of the syringe and/or cannula from a closed system. This potential withdrawal reflux can be compensated for by the positive displacement of flush solution by the stopper in the syringe assembly of the present invention.

Figure 7:
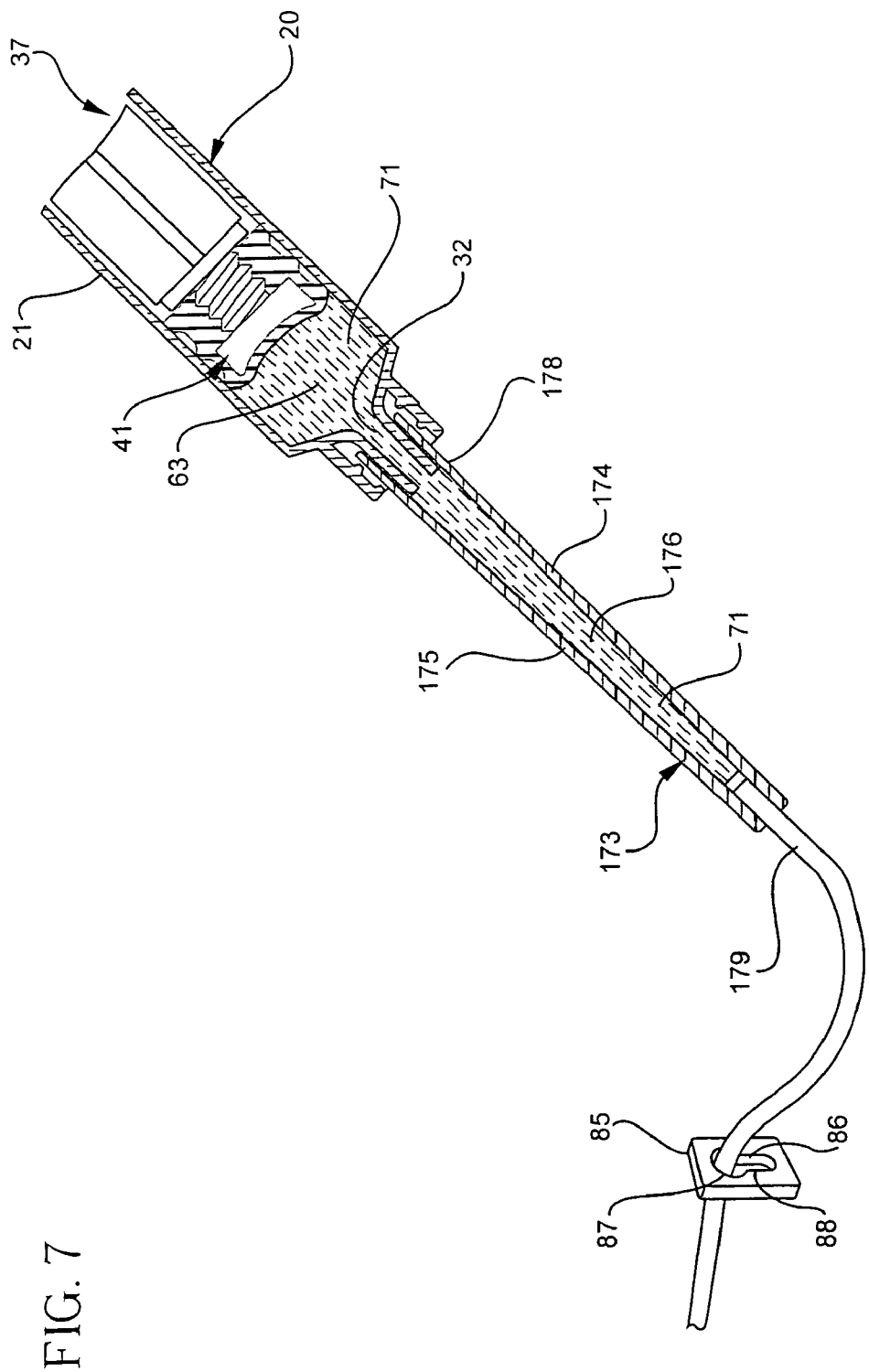
FIG. 7 is a side-elevational view illustrating the syringe assembly in use with another catheter injection site.

FIG. 7 shows an alternative simplified I.V. set to illustrate a flush procedure without a needle assembly. In FIG. 7, I.V. set 173 comprises an I.V. site 174 which includes a housing 175 having a hollow interior 176 and a luer fitting 178 at its proximal end. An I.V. line 179 having a conduit therethrough extends from the distal end of the housing. The I.V. line may be a catheter or connected to a catheter at its distal end. The I.V. set illustrated in FIG. 7 is simplified to demonstrate the invention. In most cases a luer fitting such as luer fitting 178 would be part of a one-way valve in the I.V. set. The elongate tip of the barrel is inserted and engaged with the luer fitting to establish fluid communication between interior 176 of the I.V. set and the chamber of the syringe barrel. Pressure is then applied to flange 56 on the plunger, for example by a thumb, in the distal direction. This moves plunger 37 having stopper 41 on its distal end forcing liquid such as flush solution 71 in chamber 25 out of the chamber, through passageway 32 in the elongate tip into hollow interior 176 of the I.V. set and then through I.V. line 179. The remainder of the flush procedure is substantially identical to the procedures described when using I.V. set 73 of FIG. 6. One way to clamp an I.V. line is through the use of locking member 85 which is a thin element usually made of plastic having a slot 86 therein. The slot has an enlarged portion 87 which allows flow through the I.V. line and a narrow portion 88. At the completion of the flush procedure the I.V. line is forced into the narrow portion of the slot which compresses the I.V. line to a closed configuration. Based on the experience of the person performing the flush procedure and the clinical circumstances at the time of the procedure, e.g. the patient is in an agitated state, it may be difficult to clamp the line with one hand while holding the syringe with the other hand. The present invention can allow the user to momentarily release the syringe and use two hands to clamp the I.V. line because of the syringe is still exerting a positive pressure on the flush solution as the distal wall of the stopper moves back toward its original shape.

Figure 9:
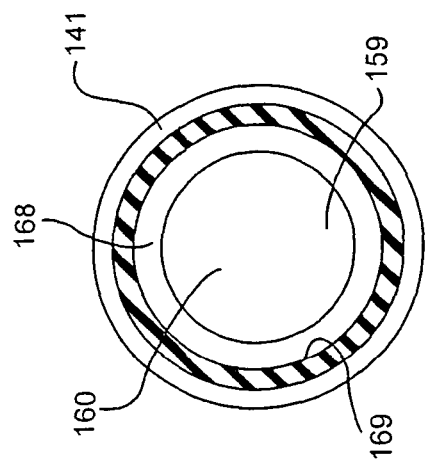
FIG. 9 is a cross-sectional view of the plunger and stopper of FIG. 8 taken along line 9-9.
Figure 8:
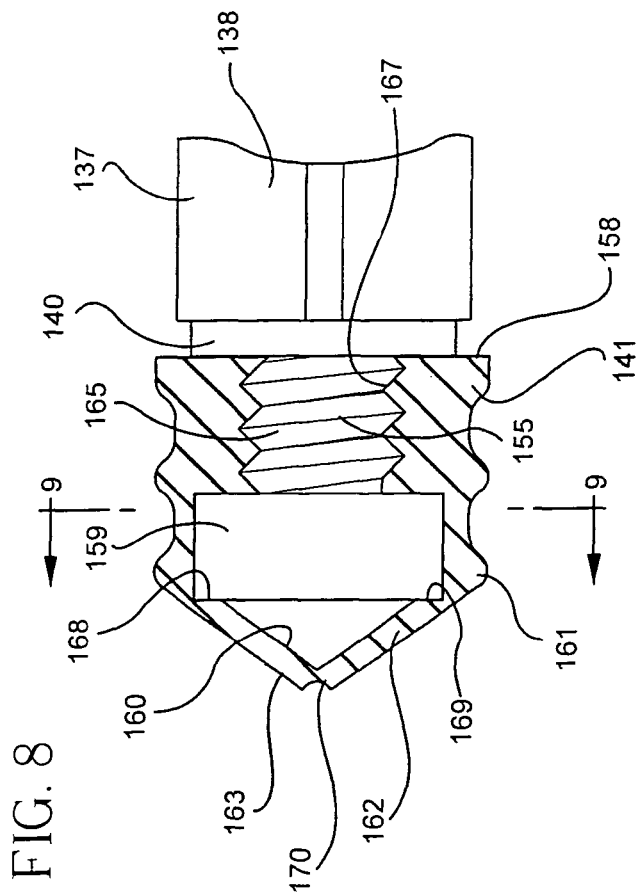
FIG. 8 is a partially cross-sectioned side-elevational view of an alternative plunger and stopper of the flush syringe assembly of the present invention.

FIGS. 8 and 9 illustrate an alternative embodiment of the plunger and stopper of the present invention. In this embodiment a plunger 137 includes an elongate body portion 138 having a distal end 140 including a distal tip 155 with an external thread 165 for engaging a stopper 141. The stopper includes a proximal end 158 having a cavity 159 therein defining an inside surface 160. A distal end 161 of the stopper includes distal wall 162 having distal surface 163. The cavity preferably includes an internal thread 167. The distal end of the plunger is connected to the stopper by action of thread 165 on the plunger and thread 167 on the stopper. In this embodiment, distal wall 162 has an area of reduced thickness to lower stiffness of the distal wall and therefore to lower the pressure required for the distal wall to collapse during the flushing procedure. In this embodiment the area of reduced thickness is provided by annular step 168 in the interior surface of distal wall 162 producing annular recess 169 which lowers the thickness of the distal wall around the entire periphery of the internal cavity. The annular recess reduces the stiffness of the distal wall and allows it to flex more easily under fluid pressure. Another area of reduced thickness in the present embodiment is distal cavity 170 on distal surface 163 of the stopper. The distal cavity also reduces the thickness of the distal wall of the stopper making it less rigid and allowing it to be more flexible in order to collapse under the fluid pressure of the flush solution during the flush procedure. Other combinations of shapes and forms to reduce the thickness of the distal wall either continuous or discreet to promote symmetric or non-symmetric collapsing of the distal wall under fluid pressure are within the purview of the present invention and the annular recess and distal cavity of the present embodiment are merely illustrative of these many possibilities.

Figure 11:
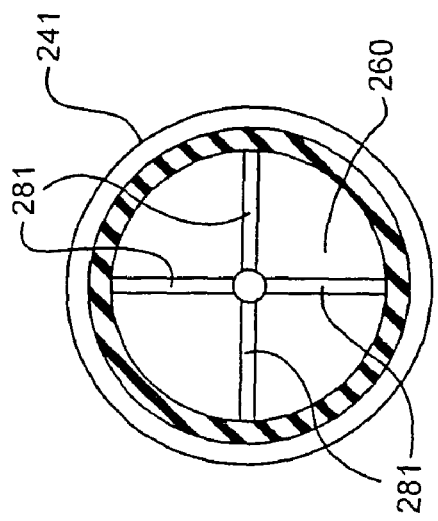
FIG. 11 is a cross-sectional view of the stopper of FIG. 10 taken along line 11-11.
Figure 10:
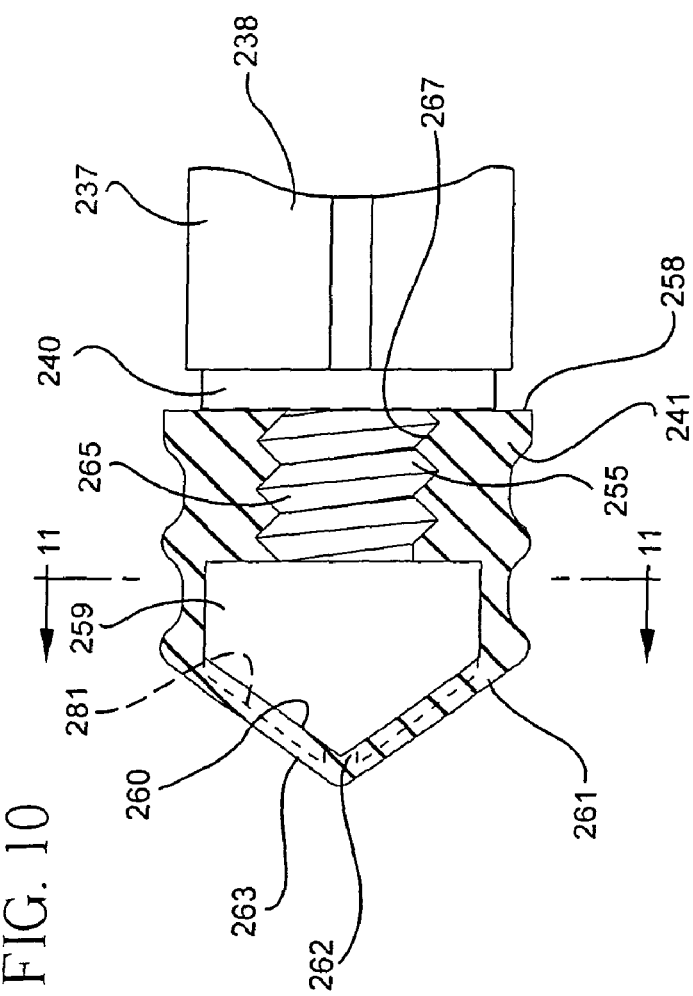
FIG. 10 is a partially cross-sectioned side-elevational view of another alternative plunger and stopper of the flush syringe assembly.

FIGS. 10 and 11 illustrate another alternative embodiment of the plunger and stopper of the present invention. In this embodiment a plunger 237 includes an elongate body portion 238 having a distal end 240 including a distal tip 255 with an external thread 265 for engaging a stopper 241. The stopper includes a distal end 261 having a cavity 259 therein defining an inside surface 260, and a proximal end 258. Distal end 261 of the stopper includes distal wall 262 having distal surface 263. The cavity preferably includes an internal thread 267. The distal end of the plunger is connected to the stopper by action of thread 265 on the plunger and thread 267 on the stopper. The stopper includes at least one rib on the inside surface of the stopper. In this embodiment raised ribs 281 on inside surface 260 of the stopper at distal wall 262 are configured to deflect when the stopper is in a collapsed position during the flush procedure and to urge the distal wall toward its original shape at the completion of the flush procedure. The raised ribs allow the use of a thinner distal wall which will be much more flexible. The raised ribs are positioned and configured to define the stiffness of the distal wall to within the chosen parameters.

Figure 14:
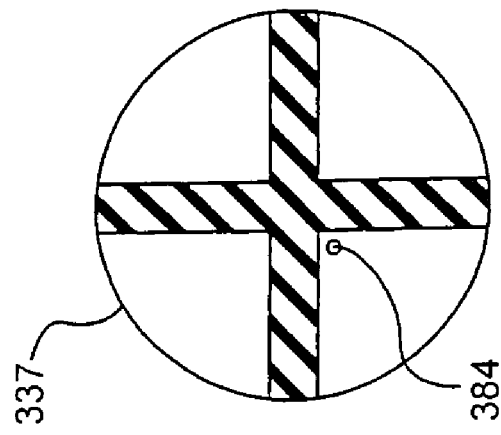
FIG. 14 is a cross-sectional view of the plunger of FIG. 12 taken along line 14-14.
Figure 13:
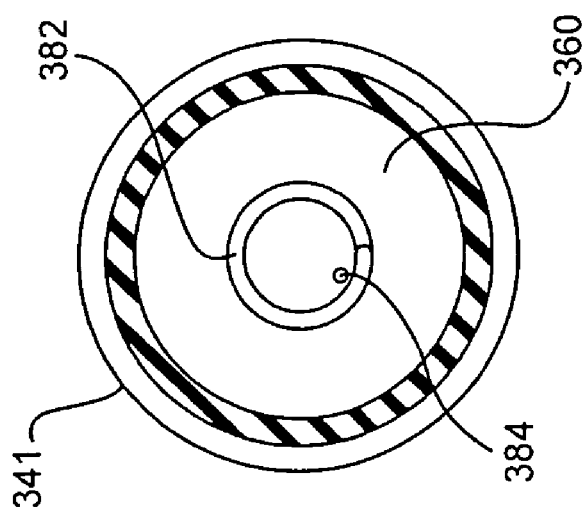
FIG. 13 is a cross-sectional view of the stopper of FIG. 12 taken along line 13-13.

FIGS. 12-14 illustrate an alternative embodiment of the plunger and stopper of the present invention. In this embodiment a plunger 337 includes an elongate body portion 338 having a distal end 340 including a distal tip 355 preferably having an external thread 365 for engaging a stopper 341. The stopper includes a distal end 361 having a cavity 359 therein defining an inside surface 360 and a proximal end 358. Distal end 361 of the stopper includes distal wall 362 having a distal surface 363. The proximal end of the stopper preferably includes an internal thread 367. The distal end of the plunger is connected to the stopper by action of thread 365 on the plunger and thread 367 in the stopper. This embodiment includes a spring 382 positioned at the inside surface of the cavity. Spring 382 is configured to compress during the flush procedures to allow the stopper to collapse and to urge the distal wall from the collapsed position toward its original shape at the end of the flush procedure. A recess 383 is provided in inside surface 360 to receive and help position the spring in the cavity. Like in the embodiment of FIGS. 8 and 9, recess 383 may also reduce the stiffness of the distal wall which increases the spring's role in determining the characteristics of the stopper during the flush procedure. This is desirable since the properties of the spring are more easily controlled and maintained than those of an elastomeric stopper. This embodiment preferably but not necessarily includes means for venting air from the stopper cavity which in this embodiment includes vent aperture 384 allowing air trapped in the stopper cavity to exit through the vent aperture and to re-enter at the end of the flush procedure when the stopper is returning to its original position from its collapsed position. By taking the trapped air which may vary from syringe to syringe out of the equation, the control of the stopper collapsing and expansion can more closely be tied to the spring and to the distal wall which may be easier to control than a random amount of air if that is the cavity of the stopper. The cavity can also be vented by an aperture or opening located in the stopper, or cooperating structure located at the interface of the stopper and the plunger or through the use of valves at one or more of these various locations. Also, a loose fit between the stopper and the plunger can function as a vent. All of these possible structures are within the purview of the present invention and the vent aperture in the plunger of this embodiment is merely representative of these many possibilities.

FIGS. 15-16 illustrate an alternative embodiment of the plunger and stopper of the present invention. In this embodiment a plunger 437 includes an elongate body portion 438 having a distal end 440 including a distal tip 455 with a radial projection 465 for engaging a stopper 441. The stopper includes a distal end 461 having a cavity 459 therein defining an inside surface 460 and a proximal end 458. A distal end 461 of the stopper includes distal wall 462 having distal surface 463. In this embodiment stopper 441 is connected to plunger 437 through the action of radial projection 465 on distal tip 455 of the plunger and recess 467 in the stopper cavity so that the stopper and the plunger engage through a snap-fit-type arrangement that may or may not be air-tight, wherein the stopper stretches over the plunger tip. There are numerous ways to attach a stopper to a plunger such as through mechanical interaction between the two elements, adhesives, ultrasonic welding, heat staking and the like. The threaded and snap-fit arrangements illustrated in the embodiments of the present invention are merely illustrative of these many possibilities all of which are within the purview of the present invention. The present embodiment further includes the inside surface of the stopper having a proximally-directed projection 482. The projection extends proximally from the distal wall and is configured to compress when the stopper is in its collapsed position and to urge the distal wall of the stopper from the collapsed position toward its original shape. The projection can be configured in many shapes such as a hollow cylinder, a spring, and an irregularly shaped projection. Proximally directed projection 482 functions in a similar manner as spring 382 in the embodiment of FIGS. 13-15.

Figure 17:
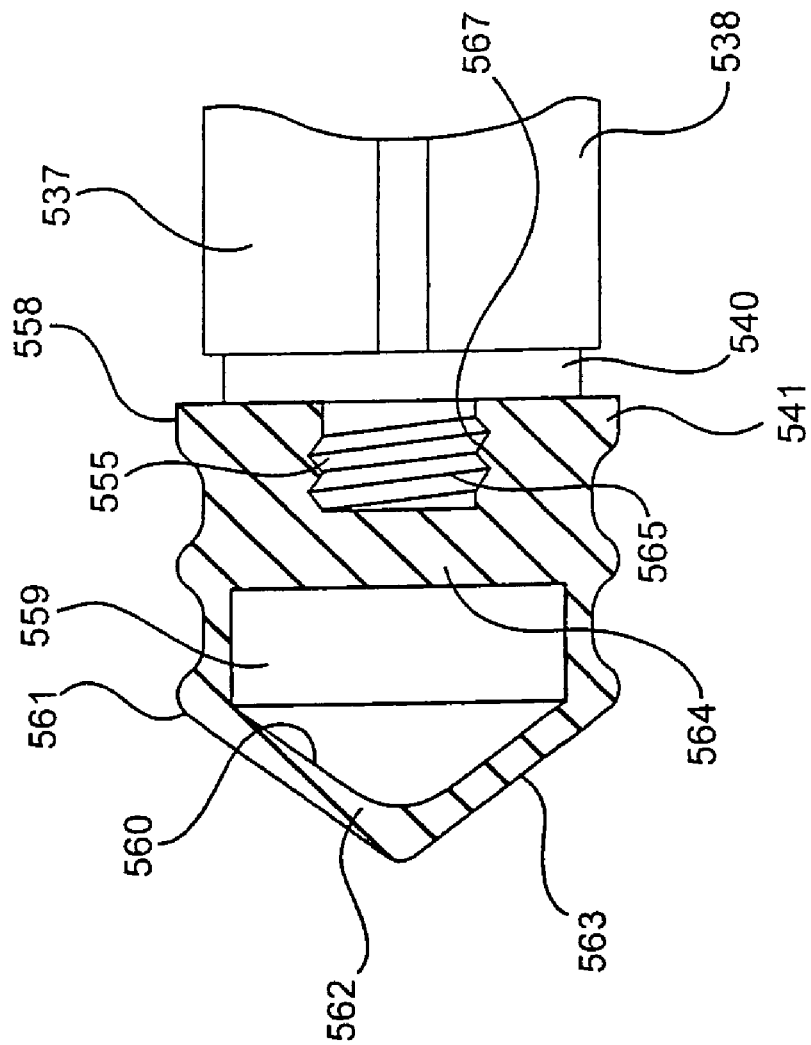
FIG. 17 is a partially cross-sectioned side-elevation view of an alternative plunger and stopper of the flush syringe assembly of the present invention.

FIG. 17 illustrates another alternative embodiment of the plunger and stopper of the present invention. In this embodiment, a plunger 537 includes an elongate body portion 538 having a distal end 540 including a distal tip 555 preferably having a an external thread 565 for engaging, a stopper 541. The stopper includes a distal end 561 having a cavity 559 therein defining an inside surface 560 and a proximal end 558. Distal end 561 of the stopper includes distal wall 562 having a distal surface 563. Proximal end 558 preferably includes internal thread 567. The distal end of the plunger is connected to the stopper by action of thread 565 on the plunger and thread 567 in the stopper. In the embodiments illustrated in FIGS. 8, 10 and 12 the distal tip of the plunger rod extends to the proximal end of the cavity in the stopper. In this embodiment proximal wall 564 blocks entry of the distal tip of the plunger rod into the cavity of the stopper. The structure may be helpful in providing a more uniform resilient stopper by controlling the air or gas pressure in the cavity more consistently from stopper to stopper.

Figure 18:
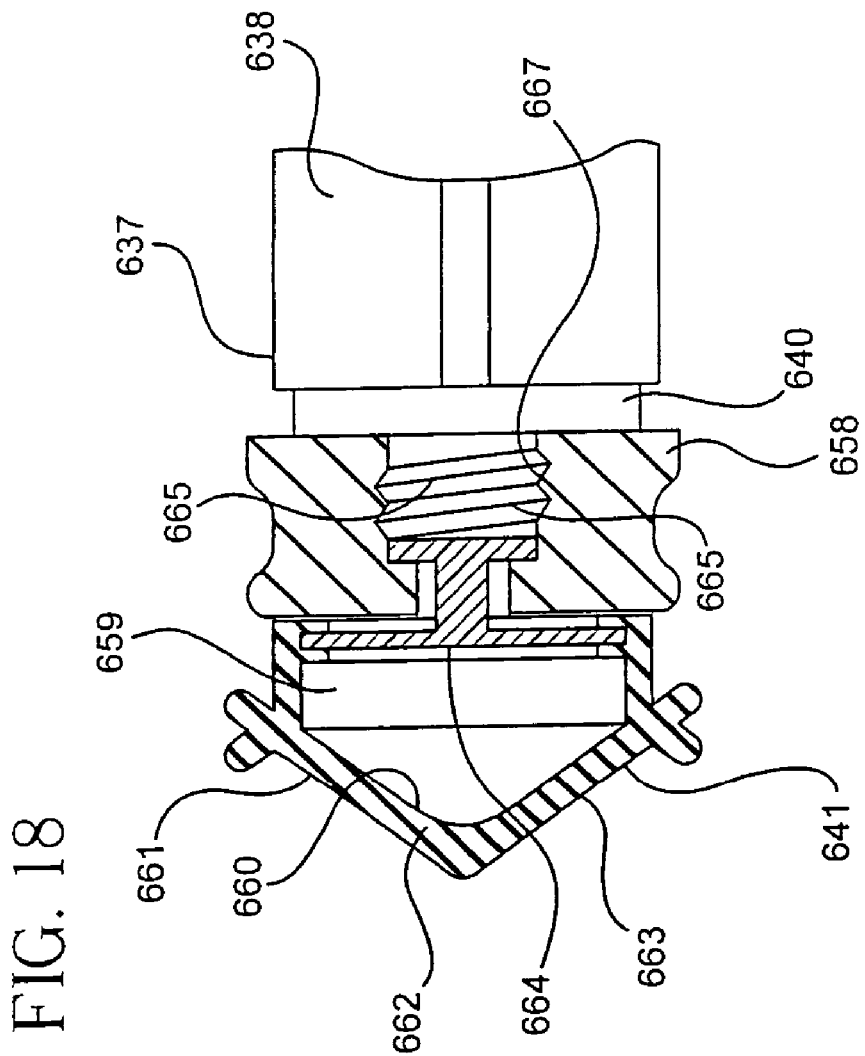
FIG. 18 is a partially cross-sectioned side-elevational view of another alternative plunger and stopper of the flush syringe assembly of the present invention.

FIG. 18 illustrates another alternative embodiment of the plunger and stopper of the present invention. In this embodiment, a plunger 637 includes an elongate body portion 638 having a distal end 640 including a distal tip 655 preferably having a thread 665 for engaging stopper 641. The stopper includes a distal end 661 having a cavity 659 therein defining an inside surface 660 and a proximal end 658. Distal end 661 of the stopper includes distal wall 662 having a distal surface 663. The proximal end of the stopper preferably includes an internal thread 667. The distal end of the plunger is connected to the stopper by action of thread 665 on the plunger and thread 667 in the stopper. This embodiment illustrates that the stopper need not be made only of one material or integrally formed. In this embodiment, the stopper comprises three elements joined together wherein distal end 661 is connected to proximal end 658 by rigid intermediate element 664. This structure allows for the proximal end and distal end of the stopper to be made of different materials and possibly through different manufacturing processes to optimize their function and tolerance control. The portions are then joined together to form a functioning stopper of the present invention.

Figure 19:
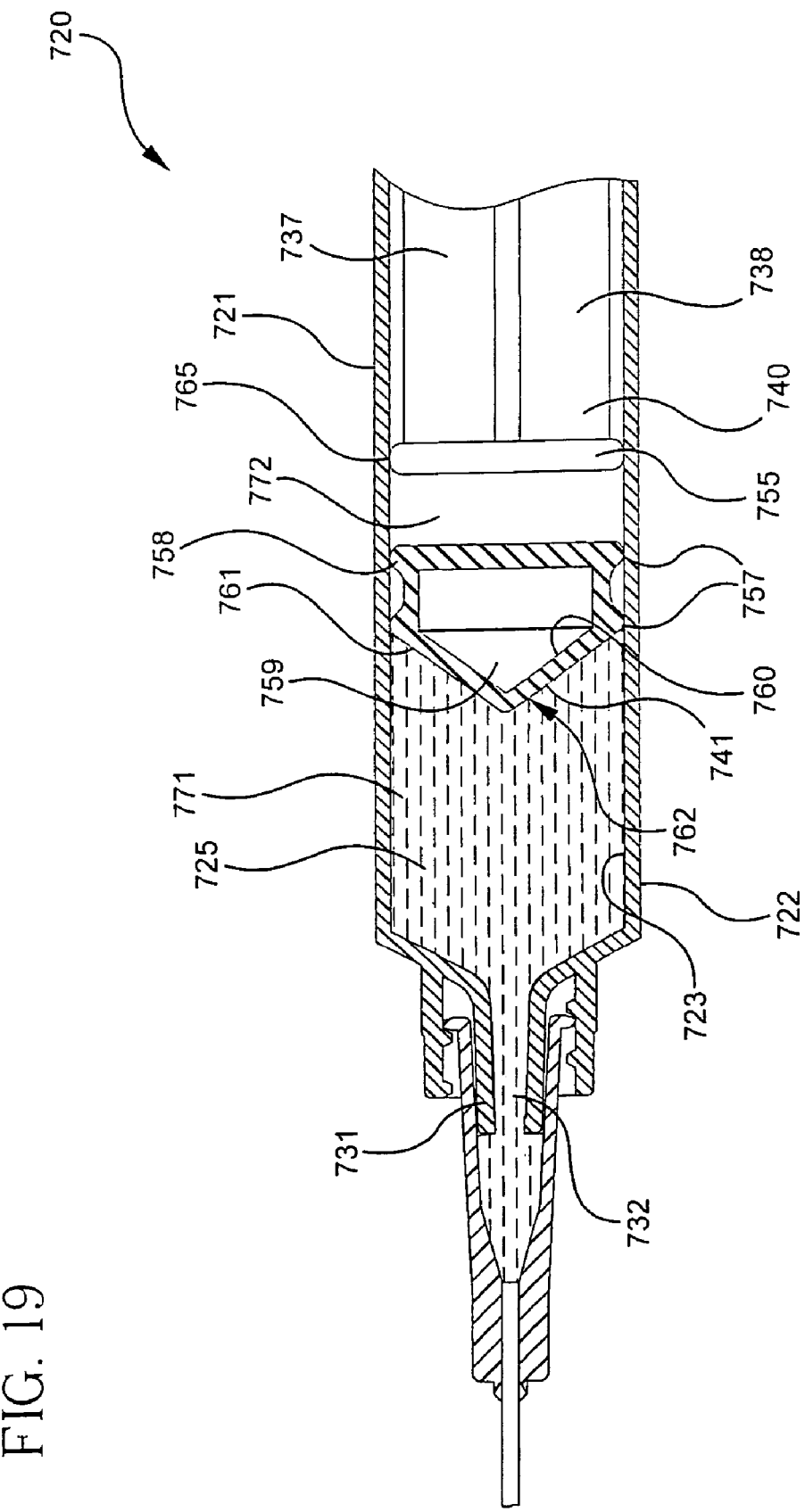
FIG. 19 is a partially cross-sectioned side-elevation view of another alternative embodiment of the syringe assembly of the present invention.

FIG. 19 illustrates another alternative embodiment of the syringe assembly of the present invention. A syringe assembly 720 according to the present embodiment generally comprises a barrel 721, including a cylindrical side wall 722 having an inside surface 723 defining a chamber 725 for retaining fluid. In this embodiment the plunger 737 includes an elongate body portion 738 having a distal end 740 including a distal tip 755 having a sealing surface 765 around its periphery in fluid-tight engagement with the inside surface of the barrel. A stopper 741 includes a distal end 761 having a cavity 759 therein defining an inside surface 760, and a proximal end 758. Distal end 761 of the stopper includes distal wall 762. As with other embodiments of the present invention, stopper 741 includes at least one rib and preferably a plurality of ribs 757 on its outside diameter. The stopper is slidably positioned in fluid-tight engagement with the inside surface of the barrel for driving fluid out of the chamber by movement of the stopper relative to the barrel. In this embodiment, the stopper is free floating relative to the plunger whereas in the embodiments of FIGS. 1-18, the stopper is connected to the plunger. In this embodiment when the plunger is moved in a distal direction the air or other gases in air space 772 between the plunger and the stopper will compress and cause the stopper to also move in a distal direction. As used herein, the term "air space" as in air space 722, is intended to mean a space between the stopper and the plunger containing a compressible gas, the gases uses in the assembly of the syringe assembly can be chosen by the manufacturer. A stopper of this embodiment performs identically to the stoppers of the embodiments of FIGS. 1-18 wherein distal wall 762 of the stopper is flexible enough to collapse at least partially into the cavity under the liquid pressure of a flush procedure and to move back toward its original shape at the completion of the flush procedure to force additional flush solution 771 into passageway 732 of elongate tip 731 of the barrel.

What is claimed is:

1. A flush syringe assembly comprising:
   a barrel including a cylindrical side wall having an inside surface defining a chamber for retaining fluid, an open proximal end and a distal end including a distal wall with a tip extending distally therefrom having a passageway therethrough in fluid communication with said chamber;
   a plunger including an elongate body portion having a proximal end and a distal end, a stopper slidably positioned in fluid-tight engagement with said inside surface of said barrel for driving fluid out of said chamber by movement of said stopper relative to said barrel, said elongate body portion extending outwardly from said open proximal end of said barrel;
   said stopper including a distal end having a distal wall and a cavity therein defining an inside surface and a proximal end, said distal wall being flexible enough to collapse at least partially into said cavity under the liquid pressure of a flush procedure and to move back toward its original shape at the completion of the flush procedure to force additional fluid into said passageway;
   said cavity including a spring at said inside surface, said spring configured to compress when said stopper is in a collapsed position and to urge said distal wall from said collapsed position toward its original shape.

2. The syringe assembly of claim 1 wherein a distal tip on said distal end of said plunger is connected to said stopper.

3. The syringe assembly of claim 1 wherein a distal tip on said distal end of said plunger includes a sealing surface around its periphery in fluid-tight engagement with said inside surface of said barrel.

4. The syringe assembly of claim 1 wherein said collapse of said distal wall occurs when said liquid pressure in said chamber is about 5 mm Hg (0.1 psi) or more.

5. The syringe of claim 1 wherein the volume of said additional fluid is about 0.001 ml or more when said syringe is connected to a peripheral catheter.

6. The syringe assembly of claim 5 wherein said additional fluid is delivered in a time of 0.5 second or more when said syringe is connected to a peripheral catheter.

7. The syringe assembly of claim 1 wherein said additional fluid is delivered in a time of 2.5 seconds or more when said syringe is connected to a peripheral catheter.

8. The syringe assembly of claim 1 wherein said stopper includes a conically shaped distal surface and said inside surface of said barrel at said distal wall is conically shaped.

9. The syringe assembly of claim 1 wherein said spring is a coil spring.

10. A flush syringe assembly comprising:
    a barrel including a cylindrical side wall having an inside surface defining a chamber for retaining fluid, an open proximal end and a distal end including a distal wall with a tip extending distally therefrom having a passageway therethrough in fluid communication with said chamber;
    a plunger including an elongate body portion having a proximal end and a distal end, a stopper slidably positioned in fluid-tight engagement with said inside surface of said barrel for driving fluid out of said chamber by movement of said stopper relative to said barrel, said elongate body portion extending outwardly from said open proximal end of said barrel;
    said stopper including a distal end having a distal wall and a cavity therein defining an inside surface and a proximal end, said distal wall being flexible enough to collapse at least partially into said cavity under the liquid pressure of a flush procedure and to move back toward its original shape at the completion of the flush procedure to force additional fluid into said passageway;
    wherein said inside surface of said stopper includes a proximally directed projection configured to compress when said stopper is in a collapsed position and to urge said distal wall from said collapsed position toward its original shape.

11. The syringe assembly of claim 1 further including means for allowing air trapped in the stopper cavity to escape as said distal wall collapses.

12. The syringe assembly of claim 11 wherein said means for air to escape includes an aperture in said plunger communicating with said cavity of said stopper.

13. The syringe assembly of claim 1 including flush solution in said chamber.

14. The syringe assembly of claim 13 wherein said flush solution is selected from the group consisting of saline flush solution and heparin lock flush solution.

15. The syringe assembly of claim 14 further including a tip cap releasably connected to said tip of said syringe barrel for sealing said passageway.

16. The syringe assembly of claim 1 wherein said stopper is made of material selected from the list consisting of thermoplastic elastomers, natural rubber, synthetic rubber, thermoplastic materials and combinations thereof.

17. The syringe assembly of claim 1 further comprising a needle assembly including a cannula having a proximal end, a distal end and a lumen therethrough, and a hub having an open proximal end, containing a cavity and a distal end attached to said proximal end of said cannula so that said lumen is in fluid communication with said cavity, said needle assembly being removably attached to said tip of said barrel through engagement of said tip to said cavity so that said lumen is in fluid communication with said chamber.

18. An I.V. flush syringe assembly comprising:
    a barrel including a cylindrical side wall having an inside surface defining a chamber for retaining fluid, an open proximal end and a distal end including a distal wall with a tip extending distally therefrom having a passageway therethrough in fluid communication with said chamber;

a tip cap releasably connected to said tip for sealing said passageway;

a plunger including an elongate body portion having a proximal end and a distal end, a resilient stopper, a quantity of flush solution in said chamber, said stopper slidably positioned in fluid-tight engagement with said inside surface of said barrel for driving fluid out of said chamber by movement of said stopper relative to said barrel, said elongate body portion extending outwardly from said open proximal end of said barrel;

structure for moving additional flush solution distally in said passageway after flush solution has been delivered from said chamber and distal motion of said plunger with respect to said barrel has stopped, including said stopper having a distal end including a distal wall and a cavity therein defining an inside surface and a proximal end, said distal wall being flexible enough to collapse at least partially, into said cavity under the liquid pressure and to move back toward its original shape at the completion of the flush procedure to force additional flush solution of at least 0.001 ml into said passageway when said syringe is connected to a peripheral catheter;

said cavity including a spring at said inside surface, said spring configured to compress when said stopper is in a collapsed position and to urge said distal wall from said collapsed position toward its original shape.

19. The syringe assembly of claim 18 wherein a distal tip on said distal end of said plunger is connected to said stopper.

20. The syringe assembly of claim 18 wherein a distal tip on said distal end of said plunger includes a sealing surface around its periphery in fluid-tight engagement with said inside surface of said barrel.

21. The syringe of claim 18 wherein said collapse of said distal wall occurs when said liquid pressure in said chamber is about 5 mm Hg (0.1 psi) or more.

22. The syringe assembly of claim 18 wherein said spring is a coil spring.

23. An I.V. flush syringe assembly comprising:

a barrel including a cylindrical side wall having an inside surface defining a chamber for retaining fluid, an open proximal end and a distal end including a distal wall with a tip extending distally therefrom having a passageway therethrough in fluid communication with said chamber;

a tip cap releasably connected to said tip for sealing said passageway;

a plunger including an elongate body portion having a proximal end and a distal end, a resilient stopper, a quantity of flush solution in said chamber, said stopper slidably positioned in fluid-tight engagement with said inside surface of said barrel for driving fluid out of said chamber by movement of said stopper relative to said barrel, said elongate body portion extending outwardly from said open proximal end of said barrel;

structure for moving additional flush solution distally in said passageway after flush solution has been delivered from said chamber and distal motion of said plunger with respect to said barrel has stopped, including said stopper having a distal end including a distal wall and a cavity therein defining an inside surface and a proximal end, said distal wall being flexible enough to collapse at least partially, into said cavity under the liquid pressure and to move back toward its original shape at the completion of the flush procedure to force additional flush solution of at least 0.001 ml into said passageway when said syringe is connected to a peripheral catheter;

wherein said inside surface of said stopper includes a proximally directed projection configured to compress when said stopper is in a collapsed position and to urge said distal wall from said collapsed position toward its original shape.

\* \* \* \* \*